United States Patent
Kim et al.

(10) Patent No.: US 12,013,384 B2
(45) Date of Patent: Jun. 18, 2024

(54) HYDROGEN SENSOR AND HYDROGEN SENSOR MANUFACTURING METHOD

(71) Applicants: Hyundai Motor Company, Seoul (KR); Kia Corporation, Seoul (KR); Industry-Academic Cooperation Foundation, Yonsei University, Seoul (KR)

(72) Inventors: Dong Gu Kim, Suwon-si (KR); Jang Hyeon Lee, Gunpo-si (KR); Dae Sung Kwon, Seoul (KR); Hyun Soo Kim, Yongin-si (KR); Il Seon Yoo, Suwon-si (KR); Tae Ho Jeong, Yongin-si (KR); Woo Young Lee, Seoul (KR); Hyun Sook Lee, Seoul (KR); Se Young Park, Seoul (KR); Soo Min Lee, Seoul (KR); Jin Kyo Jeong, Seoul (KR); Hae Won Yoon, Seoul (KR)

(73) Assignees: HYUNDAI MOTOR COMPANY, Seoul (KR); KIA CORPORATION, Seoul (KR); INDUSTRY-ACADEMIC COOPERATION FNDN, YONSEI UNIV, Seoul (KR)

( * ) Notice: Subject to any disclaimer, the term of this patent is extended or adjusted under 35 U.S.C. 154(b) by 252 days.

(21) Appl. No.: 17/807,963

(22) Filed: Jun. 21, 2022

(65) Prior Publication Data

US 2023/0130510 A1    Apr. 27, 2023

(30) Foreign Application Priority Data

Oct. 27, 2021   (KR) .......... 10-2021-0144453

(51) Int. Cl.
  *G01N 33/00*      (2006.01)

(52) U.S. Cl.
  CPC ....... *G01N 33/005* (2013.01); *G01N 33/0016* (2013.01); *G01N 2033/0019* (2013.01)

(58) Field of Classification Search
  CPC ............ G01N 33/005; G01N 33/0016; G01N 2033/0019; G01N 27/129; G01N 27/125; G01N 27/128; B82Y 15/00; B82Y 40/00
  See application file for complete search history.

(56) References Cited

U.S. PATENT DOCUMENTS

| | | | |
|---|---|---|---|
| 8,468,872 B2 * | 6/2013 | Lee .................. | G01N 33/005 73/31.03 |
| 2009/0215156 A1 * | 8/2009 | Chung ................ | B82Y 15/00 430/323 |
| 2011/0259083 A1 * | 10/2011 | Lee .................. | G01N 33/005 427/125 |

FOREIGN PATENT DOCUMENTS

| | | | | |
|---|---|---|---|---|
| EP | 2520928 A4 * | 12/2014 | ............... | B82B 3/00 |
| KR | 10-1067557 | 9/2011 | | |

(Continued)

OTHER PUBLICATIONS

Müller et al., "A quick and accurate method to determine the Poisson's ration and the coefficient of thermal expansion of PDMS", Soft Matter, 15:779-794 (2019).

(Continued)

*Primary Examiner* — Francis C Gray
(74) *Attorney, Agent, or Firm* — MCDONNELL BOEHNEN HULBERT & BERGHOFF LLP

(57) ABSTRACT

Disclosed herein is a method for manufacturing a hydrogen sensor, the method comprising the steps of: disposing a thin film made of a transition metal or an alloy thereof on a surface of elastic substrate; applying a tensile force in a repetitive manner to the elastic substrate to form a nanocrack on the thin film disposed on the surface of the elastic substrate; and injecting hydrogen gas into the formed nanoc- (Continued)

rack and then removing the hydrogen gas to form a nanogap, wherein the tensile force in the step of forming a nanocrack is applied to an extent that the elastic substrate has a tensile strain of 25% to 100%.

15 Claims, 8 Drawing Sheets

(56) References Cited

FOREIGN PATENT DOCUMENTS

| KR | 20150097871 A | * | 8/2015 | ........... G01N 33/005 |
|----|---------------|---|--------|------------------------|
| KR | 101067557 B1 | * | 9/2017 | ......... G01N 27/4146 |
| KR | 101775825 B1 | * | 9/2017 | ............... G01N 7/04 |
| KR | 101775825 B1 | | 9/2017 | |

OTHER PUBLICATIONS

Johnston, "Mechanical characterization of bulk Sylgard 184 for microfluidics and microengineering", J. Micromech. Microeng., 24:1-7 (2014).

Hübert et al., "Hydrogen sensors—A review", Sensors and Actuators B: Chemical., 157(2):329-352 (2011).

Kim et al., "Strain-controlled nanocrack formation in a Pd film on polydimethylsiloxand for the detection of H2 concentrations", Journal of Materials Science (2015).

Kim et al., "Kinetric control of nanocrack formation in a palladium thin film on an elastomeric substrate for hydrogen gas sensing in air", Sensors and Actuactors B: Chemical, 230:357-373 (2016).

* cited by examiner

HYDROGEN SENSOR AND HYDROGEN SENSOR MANUFACTURING METHOD

CROSS REFERENCE TO RELATED APPLICATIONS

This application claims the benefit of Korean Patent Application No. 10-2021-0144453, filed on Oct. 27, 2021, in the Korean Intellectual Property Office, the disclosure of which is incorporated herein by reference in its entirety.

TECHNICAL FIELD

The present disclosure relates to a hydrogen sensor and a hydrogen sensor manufacturing method and, more specifically, to a hydrogen sensor capable of detecting hydrogen gas even in the operation condition of −40° C. or lower or 150° C. or higher, and a method for manufacturing the hydrogen sensor.

BACKGROUND

As the problem environmental pollution has become a big issue, fuel cells utilizing hydrogen arise as the next-generation energy source that solves the problem, and active studies are ongoing toward the fuel cells. It is expected that hydrogen will find advantageous applications in various sectors so as to spread the hydrogen economy through hydrogen energy.

However, leakage of more than 4% of hydrogen gas into the atmosphere is at the risk of explosion, which has steadily raised the problem of stability.

Therefore, there is a need for the development of a hydrogen sensor capable of early detection of the leakage of hydrogen gas in order to perfectly utilize hydrogen energy.

Among the hydrogen sensors developed thus far are ceramic-type hydrogen sensors such as catalytic combustion-type hydrogen sensors, hot wire-type hydrogen sensors, and thermoelectric hydrogen sensors; semiconductor-type hydrogen sensors such as thick film semiconductor-type hydrogen sensors and thin film semiconductor-type hydrogen sensors; electrochemical hydrogen sensors such as potentiometric hydrogen sensors, amperometric hydrogen sensors, and solid electrolyte hydrogen sensors; and metal absorption-type hydrogen sensors such as Pd resistance-type hydrogen sensors, Pd detection-type hydrogen sensors, and Pd SAW hydrogen sensors. Korean Patent Number 10-1067557 discloses a method for manufacturing a hydrogen sensor of high performance in a Pd thin film sensor form, wherein a thin film, made of a transition metal or an alloy thereof, having a uniform nanogap is arranged on a substrate by applying a physical tensile force to the substrate. Korean Patent Number 10-1775825 discloses a method for controlling overall density and average width of nanogaps according to tension-compression rates and tension and compression strains.

The foregoing is intended merely to aid in the understanding of the background of the present disclosure, and is not intended to mean that the present disclosure falls within the purview of the related art that is already known to those skilled in the art.

SUMMARY

The present disclosure is to provide a hydrogen sensor available for a hydrogen vehicle, which uses hydrogen fuel for motive power, wherein the hydrogen sensor can detect 0.1% to 4% of hydrogen gas within a short time and can normally operate even in an extreme condition which the hydrogen vehicle may encounter, for example, an extremely low temperature such as −40° C., or a high temperature such as 150° C. to which the internal temperature of the vehicle can increase while the vehicle drives.

To achieve the goal, the present disclosure provides a method for manufacturing a hydrogen sensor, the method including the steps of disposing a thin film made of a transition metal or an alloy thereof on a surface of elastic substrate; applying a tensile force in a repetitive manner to the elastic substrate to form a nanocrack on the thin film disposed on the surface of the elastic substrate; and injecting hydrogen gas into the formed nanocrack and then removing the hydrogen gas to form a nanogap, wherein the tensile force in the step of forming a nanocrack is applied to an extent that the elastic substrate has a tensile strain of 25% to 100%.

The nanogap formed may range in width from 30 nm to 200 nm.

The thin film disposed on the surface of the elastic substrate may be 10 nm or more in thickness.

The thin film disposed on the surface of the elastic substrate may be 20 nm or more in thickness.

The transition metal may be at least one selected from the group consisting of Pd, Pt, Ni, Ag, Ti, Fe, Zn, Co, Mn, Au, W, In, and Al.

The alloy may be at least one selected from the group consisting of Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ag, Pt—Ti, Fe—Pt, Pt—Zn, Pt—Co, Pt—Mn, and Pt—Au, Pt—W.

The transition metal may be Pd and the alloy may be a Pd-based alloy.

The elastic substrate may use a natural rubber, a synthetic rubber, or a polymer.

The synthetic rubber may be any one selected from the group consisting of a butadiene-based rubber, an isoprene-based rubber, a chloroprene-based rubber, a nitrile-based rubber, a polyurethane-based rubber, and a silicone-based rubber.

The silicone-based rubber may be PDMS (polydimethylsiloxane).

PDMS may be prepared after being cured at 150 to 200° C. for 5 minutes to 10 minutes, or PDMS may be prepared after being cured at 10 to 25° C. for 24 hours to 48 hours and then at 50 to 75° C. for 30 minutes to 240 minutes.

The elastic substrate may have a Young's modulus of 0.5 MPa to 2.6 MPa, a tensile strength of 5 MPa to 7 MPa, an elongation of 100% to 200%, and a coefficient of thermal expansion of 270 to 340 ppm/° C.

The elastic substrate may have a Young's modulus of 2.5 MPa to 4.0 MPa, a tensile strength of 3 MPa to 5 MPa, an elongation of 100% to 200%, and a coefficient of thermal expansion of 200 to 250 ppm/° C.

In the step of forming a nanocrack, the tensile force may be applied 12 to 24 times repetitively.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION

The present disclosure may be variously modified and include various exemplary embodiments in which specific exemplary embodiments will be described in detail hereinbelow. However, it shall be understood that the specific exemplary embodiments are not intended to limit the present disclosure thereto and cover all the modifications, equivalents and substitutions which belong to the idea and technical scope of the present disclosure.

The present disclosure is to provide a hydrogen sensor manufacturing method wherein the hydrogen sensor is suitable for a hydrogen fuel cell vehicle using hydrogen energy as motive power and can detect leakage hydrogen even in the temperature range from −40° C. to 150° C. in light of the seasonal climate of Korea.

Figure 1:
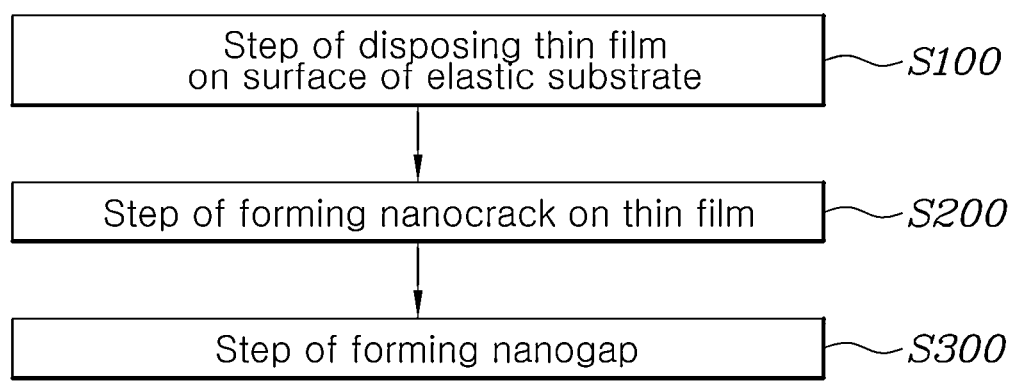
FIG. 1 is a flow scheme of a hydrogen sensor manufacturing method according to an embodiment of the present disclosure.
Figure 2:
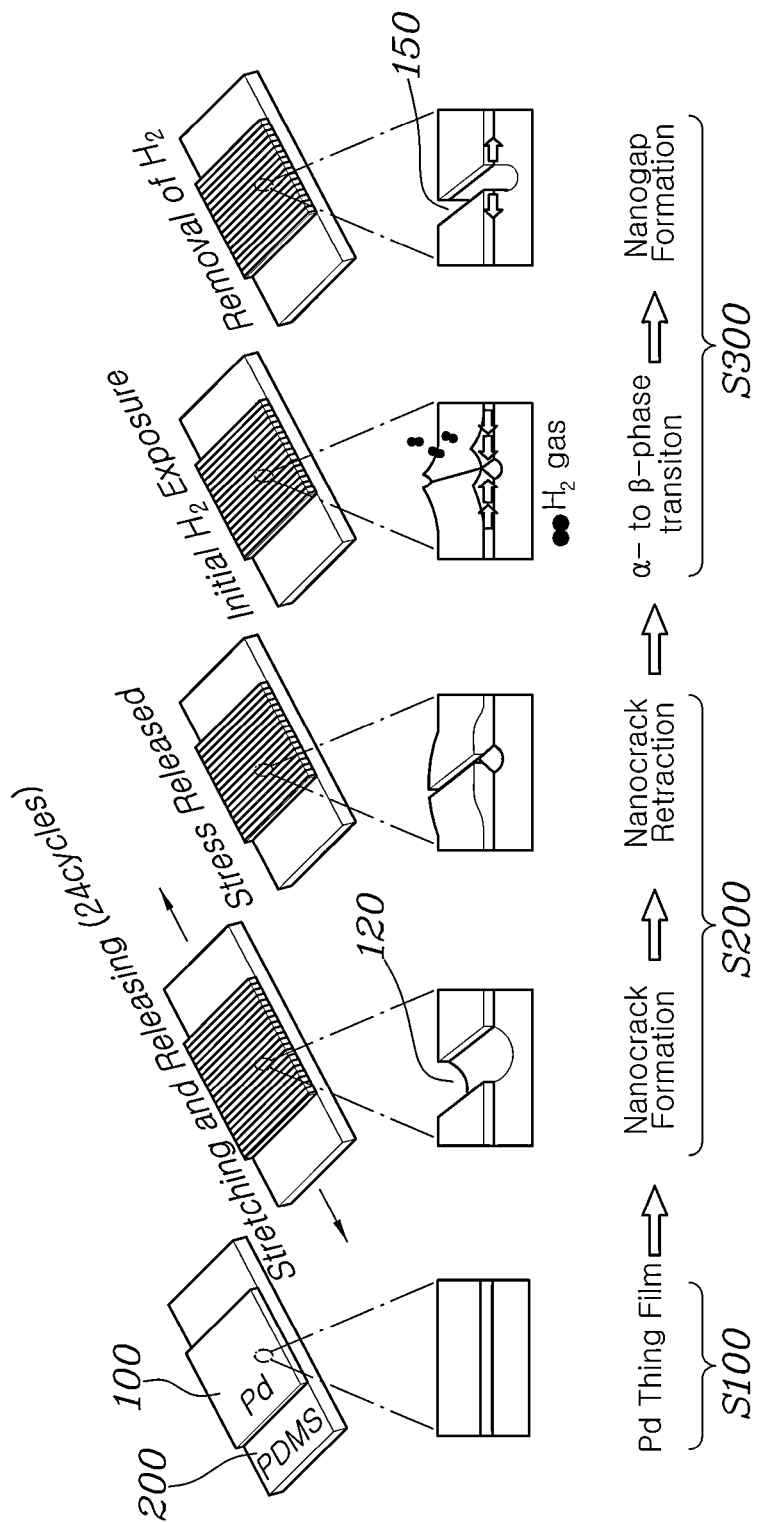
FIG. 2 shows illustrations of a hydrogen sensor manufacturing method according to an embodiment of the present disclosure.

FIG. 1 is a flow scheme of a hydrogen sensor manufacturing method according to an embodiment of the present disclosure and FIG. 2 shows illustrations of a hydrogen sensor manufacturing method according to an embodiment of the present disclosure. Referring to the figures, the hydrogen sensor manufacturing method according to an embodiment of the present disclosure includes the steps of disposing a thin film 100 of a transition metal or an alloy thereof on a surface of an elastic substrate 200 (S100); forming a nanocrack 120 on the thin film 100 disposed on a surface of the elastic substrate 200 (S200); and inject hydrogen gas into the formed nanocrack 120 and then removing the hydrogen gas to form a nanogap 150 (S300).

The hydrogen sensor manufactured according to the present disclosure detects hydrogen through the nanogap 150 formed in the thin film 100 of a transition metal or an alloy thereof. Before the nanogap 150 absorbs hydrogen, the thin film 100 of a transition metal or an alloy thereof has a high resistance due to the nanogap 150. The nanogap formed in the thin film absorbs hydrogen in a hydrogen atmosphere. Accordingly, the thin film 100 of a transition metal or an alloy thereof increases in lattice constant and the nanogap is filled, with the concomitant smooth flow of currents, which leads to reducing the resistance in the thin film. Through this mechanism, hydrogen can be detected. Furthermore, even the concentration of the leaked hydrogen gas can be determined by measuring a change of the resistance value.

Conventional modes (such as contact combustion type, etc.) are disadvantageous in that water is formed on the surface of a detection portion as a result of the reaction between hydrogen and oxygen and forms ice crystals at sub-zero temperatures, causing the hydrogen sensor to falsely operate. In contrast, the hydrogen sensor according to the mode of the present disclosure does not suffer from the disadvantage because no water is generated.

Furthermore, conventional modes require high consumption power for hydrogen detection because the surface of the detection portion is established in a high-temperature condition, so that the hydrogen sensors are difficult to derive with the battery equipped in the vehicle. In contrast, the hydrogen sensor according to the mode of the present disclosure can be operated with a low power because a high temperature condition is not needed.

The hydrogen sensor manufacturing method according to an embodiment of the present disclosure does not adopt MEMS processes such as lithography and is designed to dispose a thin film of a transition metal or an alloy thereof on an elastic substrate and apply a tensile force to the elastic substrate to form a nanogap, whereby hydrogen sensors can be produced at low cost, compared to conventional methods.

As illustrated in FIG. 2, a thin film 100 of a transition metal or an alloy thereof is disposed on a surface of an elastic substrate 200, followed by repetitively applying a tensile force to the elastic substrate 200 as in step S200 to form a nanocrack 120, which is a nano-sized groove. The repetitive application of a tensile force as in step S200 subjects the nanocrack 120 to cycles of formation and retraction, resulting in increasing the size of the nanocrack 120. After the repetitive application of a tensile force, injection of 2% of hydrogen gas into the nanocrack 120 formed in the elastic substrate 200 and the thin film 100 induces alpha- to beta-phase transition. By removing the hydrogen gas, a nanogap 150 is formed.

In the step of forming a nanogap 150 (S200), the tensile force may be applied in a controlled manner so that the elastic substrate 200 has a tensile strain of 25% to 100%. As shown in FIG. 2, when a tensile force is applied to the elastic substrate 200 in the left and right direction, the thin film 100 is stretched in the left and right direction while being contracted in the vertical direction. Retraction of the tensile force applied makes the thin film 100 contract in the left and right direction and simultaneously stretch in the vertical direction, with the consequent formation of a nanocrack.

The tensile force in the step of forming a nanocrack 120 (S200) may be repetitively applied 12 to 24 times.

In this regard, the term "tensile strain of 25% to 100%" means that if the elastic substrate 200 is 100 cm long the tensile force is applied to such an extent as to extend the elastic substrate 200 to a length of 125 cm to 200 cm.

No limitations are imparted to kinds of the transition metal used in the present disclosure. So long as it allows the formed nanogap 150 to be filled with hydrogen gas, any transition metal or an alloy thereof may be used as the constituent of the thin film.

In a particular embodiment, the transition metal may be at least one selected from the group consisting of Pd, Pt, Ni, Ag, Ti, Fe, Zn, Co, Mn, Au, W, In, and Al and the transition metal alloy may be at least one selected from the group consisting of Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ag, Pt—Ti, Fe—Pt, Pt—Zn, Pt—Co, Pt—Mn, Pt—Au, and Pt—W.

Most particularly, the transition metal and the alloy thereof are Pd and an alloy containing same, respectively.

So long as it can stretch in the direction corresponding to the application of a tensile force to the elastic substrate 200 and contract back to the original state upon retraction of the tensile force, any material may be used for the elastic substrate 200. Examples of the material available for the elastic substrate include a natural rubber, a synthetic rubber, and a polymer.

For use in preparing the elastic substrate 200, the synthetic rubber may be selected from the group consisting of butadiene-based rubbers, isoprene-based rubbers, chloroprene-based rubbers, nitrile-based rubbers, polyurethane-based rubbers, and silicone-based rubbers. Particularly available is PDMS (polydimethylsiloxane), which is a material that makes it convenient to mold the transition metal or the alloy thereof disposed on the substrate due to the low contact free energy and is superb in terms of durability.

Any method that is used in the art may be employed to dispose the thin film of a transition metal or an alloy thereof on the elastic substrate 200, as representatively exemplified by physical deposition such as evaporation, sputtering, etc., or chemical deposition such as chemical vapor deposition, atomic layer deposition, etc.

The nanogap 150 formed in the thin film 100 vary in width size depending on the tensile force applied to the elastic substrate 200. With reference to panel (a) of FIG. 3, when a tensile force was repetitively applied so as to achieve a tensile strain of 100%, the nanogap 150 was observed to have a width of 32.8 nm in the direction (hereinafter referred to as "y-axis direction") perpendicular to the application direction of the tensile force and a width of 11.3 nm in the application direction of the tensile force (hereinafter referred to as "x-axis direction").

Figure 3:
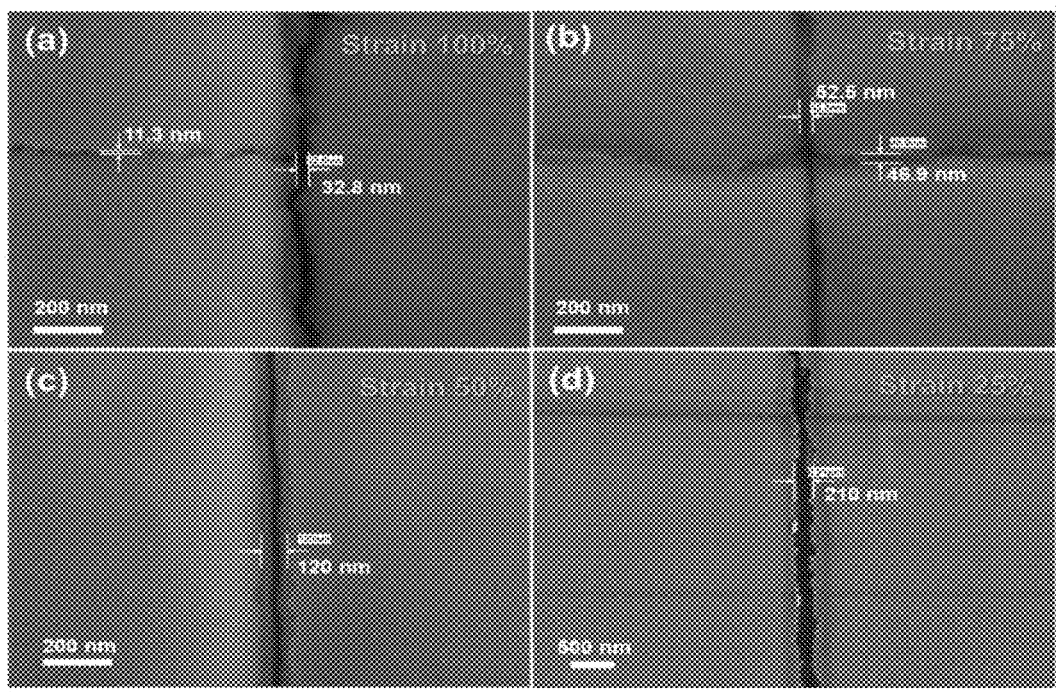
FIG. 3 shows images of nanogaps formed at various sizes on thin films when a tensile force is repetitively applied to an extent that the tensile strain reaches 100%, 75%, 50%, and 25%.

Referring to panel (b) of FIG. 3, when a tensile force was repetitively applied so as to achieve a tensile strain of 75%, the nanogap 150 was observed to have a width of 52.5 nm in y-axis direction and a width of 46.9 nm in x-axis direction. As shown in panel (c) of FIG. 3, when a tensile force was repetitively applied so as to achieve a tensile strain of 50%, the nanogap 150 was observed to have a width of 120 nm in y-axis direction. For the repetitive application of a tensile strength to an extent of a tensile strain of 25%, the nanogap 150 was observed to have a width of 210 nm as shown in panel (d) of FIG. 3.

The size of nanogap 150 is closely related with hydrogen detection capacity. If its size is too large, the nanogap 150, although absorbing hydrogen, is difficult to completely fill with leaked hydrogen. Under this condition, the resistance change is small, leading to a poor hydrogen detection capacity. At an extremely low temperature (−40° C.), the elastic substrate 200 is contracted so that the nanogap 150 formed in the thin film 100 may be closed with its size being reduced. Thus, the size of the nanogap 150 formed in the thin film 100 should be optimized.

Figure 4A:
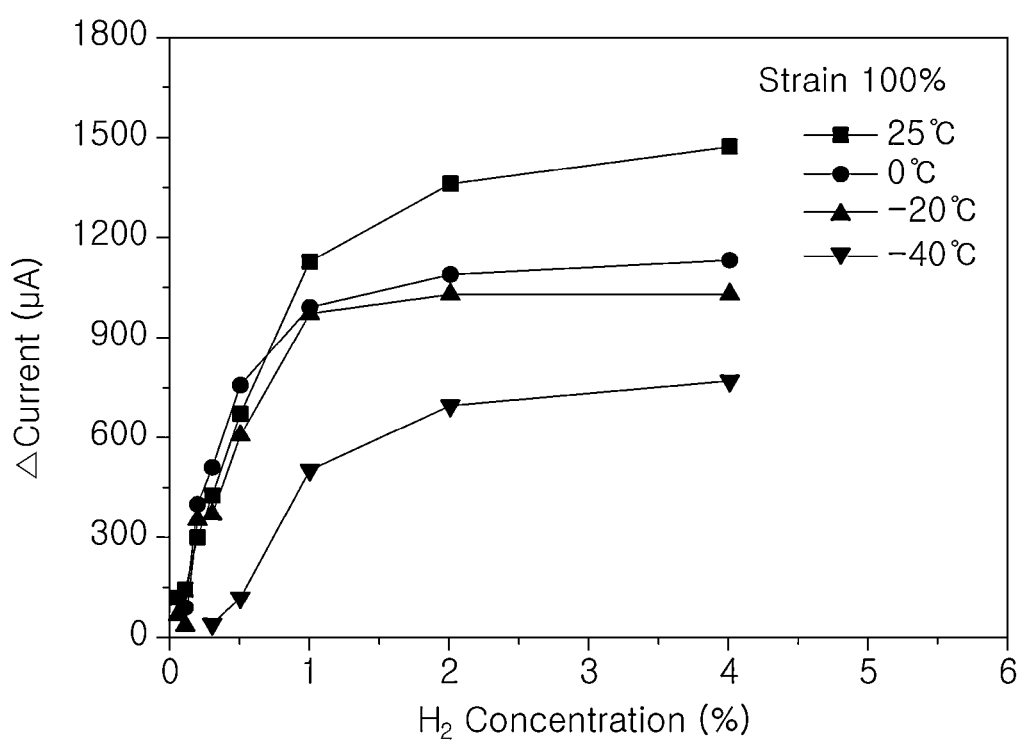
FIGS. 4A to 4D show plots obtained from an assay for hydrogen detection at room temperature or low temperatures according to magnitudes of the tensile strain.

FIGS. 4A-4D shows plots obtained from an assay for hydrogen detection at room temperature or low temperatures according to magnitude of the tensile strain. With reference to FIG. 4A, when a tensile strain of 100% is given, the greatest current change was detected at room temperature in sensitive response to hydrogen, accounting for excellent detection performance. However, the reactivity remarkably decreased with decreasing of the temperature. This is considered to be attributed to the fact that the nanogap with a size of 30 nm is closed due to the contraction of the elastic substrate at low temperatures.

Figure 4B:
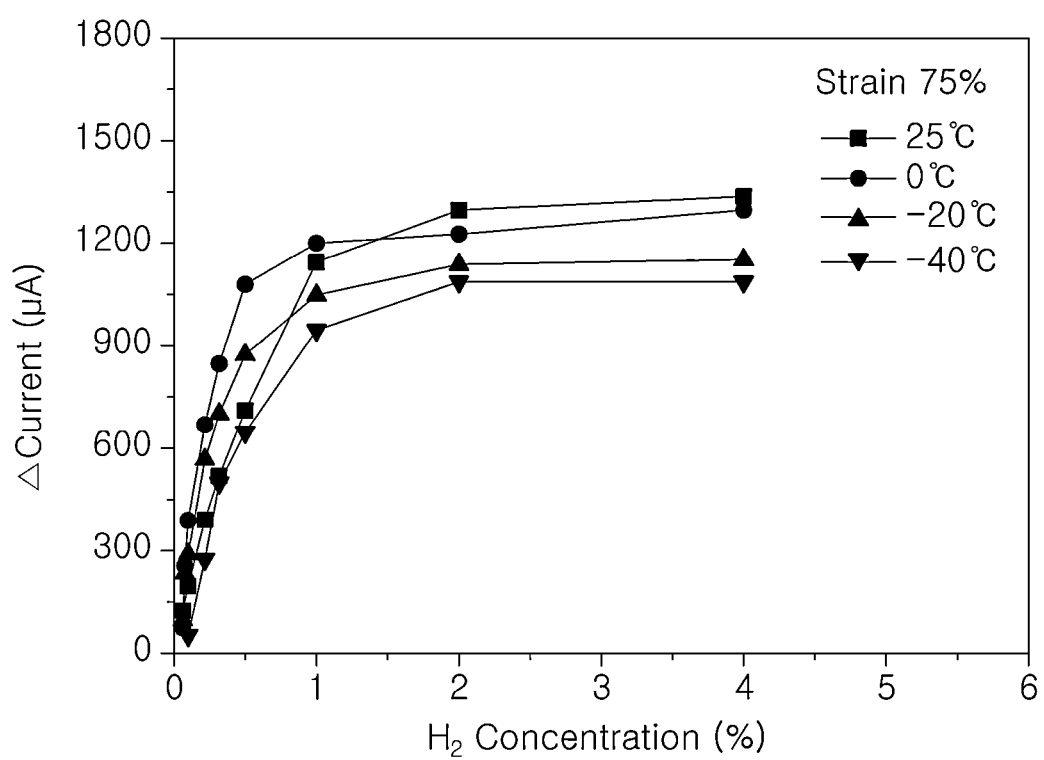
Figure 4C:
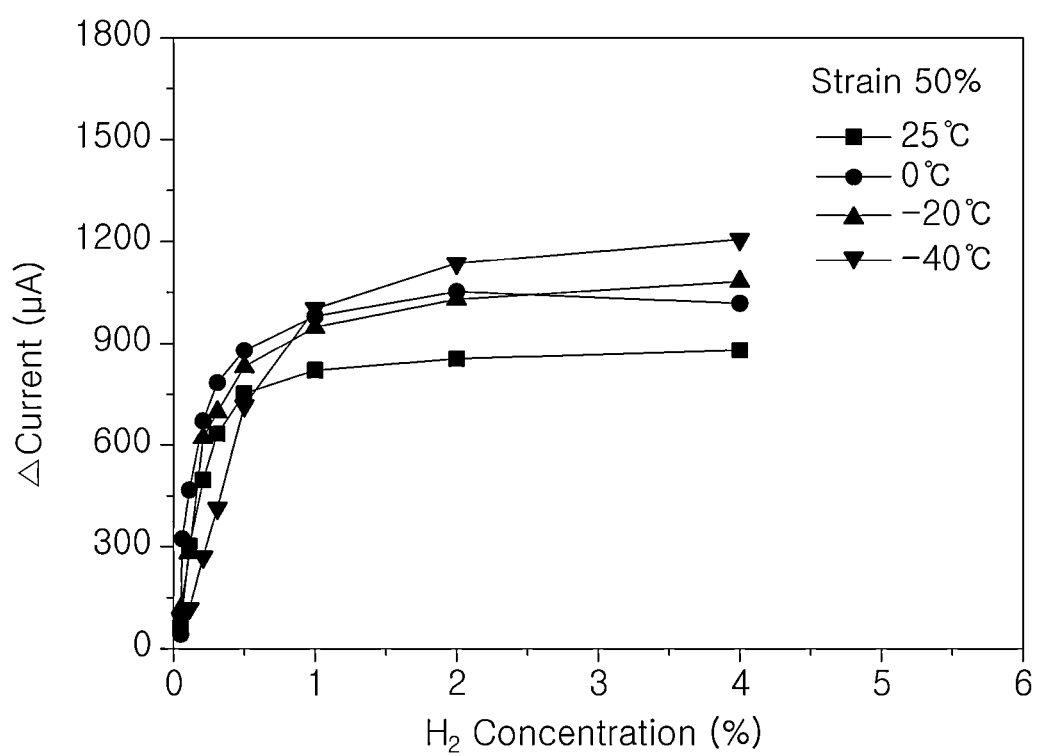
Figure 4D:
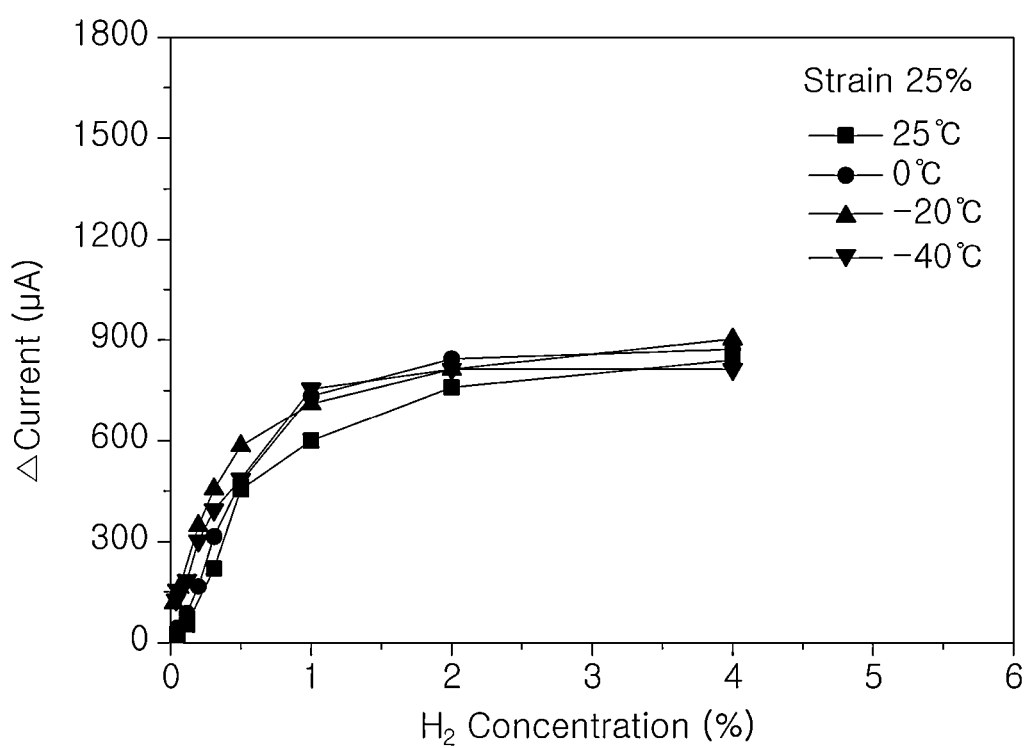

Referring to FIG. 4B, similar levels of reactivity are detected irrespective of temperatures for a tensile strain of 75%, with the slightly largest current change detected at room temperature. Referring to FIG. 4C, more sensitive responses are observed at low temperatures than room temperature for a tensile strain of 50% because the size of the nanogap is reduced to 120 nm or less at low temperatures. Referring to FIG. 4D, similar levels of reactivity are detected irrespective of temperatures for a tensile strain of 25%.

The nanogap 30 nm or less in size at room temperature tends to be closed at low temperatures. Thus, the nanogap 150 preferably has a size of 30 nm or higher at room temperature. A nanogap 150 with a size greater than 120 nm cannot detect less than 0.1% of hydrogen gas although its size decreases with the contraction of the elastic substrate in a low-temperature conditions. Hence, the size of the nanogap 150 is preferably 120 nm or less at room temperature.

The elastic substrate for use in the sensor for hydrogen detection at room temperature, for example, PDMS may be prepared by being cured at 10° C. to 25° C. for 24 hours to 48 hours and then at 50° C. to 75° C. for 30 minutes to 240 minutes so as to meet a Young's modulus of 0.5 MPa to 2.6 MPa, a tensile strength of 5 MPa to 7 MPa, an elongation of 100% to 200%, and a coefficient of thermal expansion of 270 to 340 ppm/° C.

The tension condition is preferably set to be 400-800 μm/s for tension-compression speed and 50-100% for tension-compression strain, with 24 cycles of tension and compression.

When the Young's modulus, tensile strength, and elongation are below or over the ranges given thereto, the nanogap is difficult to form and control through tension. In detail, when the tension conditions are below the lower limits of the corresponding ranges, the nanogap 150 is formed to have a size of 1 μm or more and as such, is unable to detect hydrogen. Under the tension conditions exceeding the upper limits of the corresponding ranges, the ductility becomes poor so that tension is impossible.

At a coefficient of thermal expansion of less than 250 ppm/° C., the elastic substrate 200 is prone to undergoing less contraction in a low-temperature condition and accordingly, the nanogap 150 undergoes less reduction in size and is unable to detect 0.1% or less of hydrogen gas. At a coefficient of thermal expansion exceeding 340 ppm/° C., the elastic substrate undergoes large contraction in low-temperature conditions. As a result, the nanogap reduces in size too excessively and is finally closed, exhibiting poor performance of detecting 4% or higher of hydrogen gas.

Meanwhile, the nanogap 150 increases in size at a temperature higher than 60° C. because the elastic substrate 200 expands. In order to restrain the size increase of the nanogap 150 with temperature elevation, the thin film 100 disposed on the surface of the elastic substrate 200 is preferably formed to have a thickness of 20 nm or greater (hydrogen sensor adapted to low temperatures may be about 10 nm thick without taking the size increase into consideration, but may also be provided with a thickness of 20 nm or more in order to reduce the contraction with a temperature change).

The elastic substrate for use in the sensor for hydrogen detection at high temperatures, for example, PDMS may be prepared by being cured at 150° C. to 200° C. for 5 minutes to 10 minutes so as to meet a Young's modulus of 2.5 MPa to 4.0 MPa, a tensile strength of 3 MPa to 5 MPa, an elongation of 100% to 200%, and a coefficient of thermal expansion of 200 to 250 ppm/° C. When the curing temperature for PDMS is increased from 75° C. to 150° C., the coefficient of thermal expansion of the PDMS cured at the high temperature is lower than that of the PDMS cured at the low temperature so that the size increase of the nanogap attributed to the expansion of PDMS can be restrained. Thus, the hydrogen sensor can retain the hydrogen detection capacity even in a high-temperature condition (the CTE of the cured PDMS is decreased with increasing of the curing temperature from 75° C. to 200° C. so that the size increase of the nanogap attributed to the expansion of PDMS can be restrained. Thus, the hydrogen sensor can retain the hydrogen detection capacity even in a high-temperature condition:

309 ppm/° C. at 25° C., 277 ppm/° C. at 75° C., 261 ppm/° C. at 100° C., 196 ppm/° C. at 200° C.).

The tension condition is preferably set to be 400-800 µm/s for tension-compression speed and 50-100% for tension-compression strain, with 12-24 cycles of tension and compression.

When the Young's modulus, tensile strength, and elongation are below or over the ranges given thereto, the nanogap is difficult to form and control through tension. In detail, when the tension conditions are below the lower limits of the corresponding ranges, the nanogap 150 is formed to have a size of 1 µm or more and as such, is unable to detect hydrogen. Under the tension conditions exceeding the upper limits of the corresponding ranges, the ductility becomes poor so that tension is impossible.

At a coefficient of thermal expansion of less than 200 ppm/° C., the elastic substrate 200 is prone to undergoing less expansion in a high-temperature condition and accordingly, the nanogap 150 undergoes less reduction in size and is unable to expand over 200 nm. At a coefficient of thermal expansion exceeding 250 ppm/° C., the size of the elastic substrate increases over 200 nm with the expansion of the elastic substrate 200 under a high temperature condition. As a result, the nanogap exhibits poor performance of detecting 4% or higher of hydrogen gas.

Figure 5:
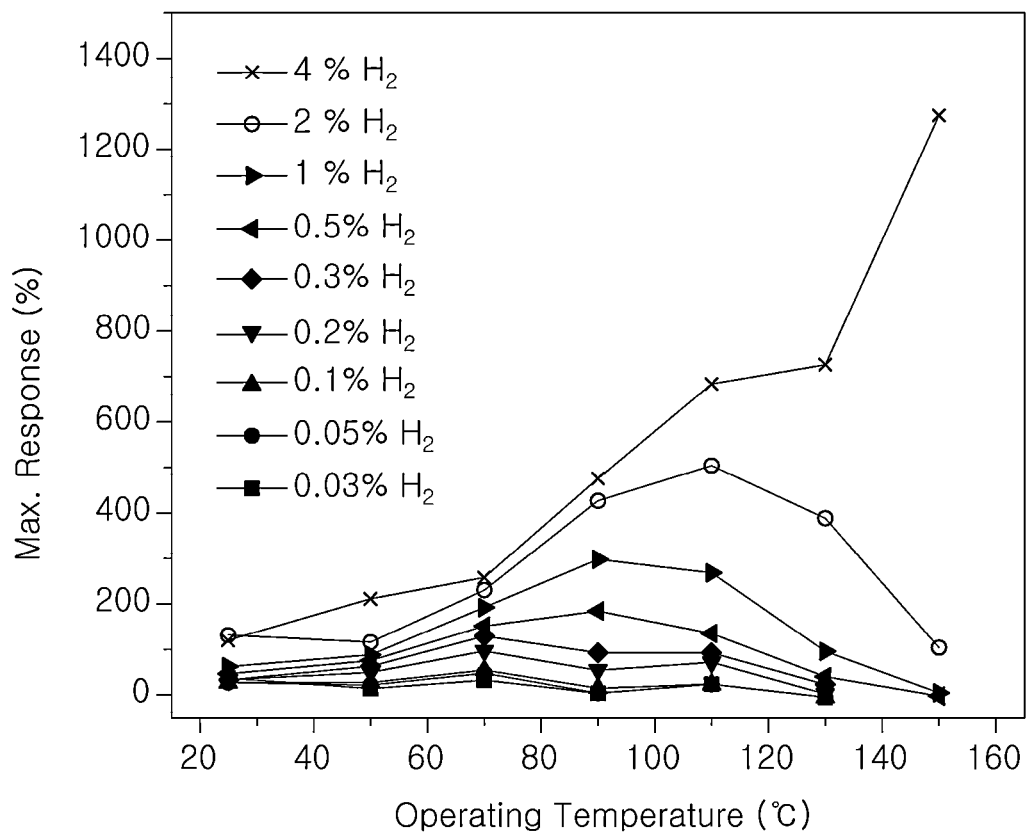
FIG. 5 is a plot obtained from an assay for hydrogen detection of a hydrogen sensor manufactured at a high temperature with a tensile strain set to be 50%.

FIG. 5 is a plot obtained from an assay for hydrogen detection of a hydrogen sensor manufactured at a high temperature with a tensile strain set to be 50%. Referring to FIG. 5, it was observed that the hydrogen sensor can detect 4% of hydrogen gas at the high temperature of 150° C. and responds to even as low as 0.03% of hydrogen gas at the high temperature of 130° C.

The hydrogen sensor manufactured according to the present disclosure does not necessarily require a high-temperature operation environment and as such can drive with low power. When applied to a hydrogen fuel cell vehicle, the hydrogen sensor can detect hydrogen leakage even in a driving-off condition. The hydrogen sensor manufacturing method according to the present disclosure is designed to form a nanogap through controlling a tensile strain and a tensile force without employing MEMS processes such as lithography, whereby hydrogen sensors can be produced at low cost, compared to conventional methods. Hydrogen sensors are suitable for driving at low temperatures, with the nanogap ranging in size from 50 nm to 120 nm, at both low and high temperatures, with the nanogap ranging in size from 100 to 120 nm, and at high temperatures, with the nanogap ranging in size from 100 to 200 nm.

Although the forms of the present disclosure have been disclosed for illustrative purposes, those skilled in the art will appreciate that various modifications, additions and substitutions are possible, without departing from the scope and spirit of the present disclosure.

As described hitherto, according to the hydrogen sensor and the hydrogen sensor manufacturing method of the present disclosure, there are the advantages of being able to stably detect leaked hydrogen even in the condition of extremely low temperature (−40° C.) or 150° C.; solving a problem of conventional hydrogen sensors that their sensing performance is lowered as the water molecules formed on the hydrogen sensors are frozen at 0° C. or less; being able to drive with a low power because the substrate for detecting hydrogen gas does not need to be manufactured in a high-temperature state; and manufacturing the hydrogen sensor at a low cost compared to conventional hydrogen sensors because the nanogap can be formed by controlling the tensile strain without a complicated process such as lithography.

What is claimed is:

1. A method for manufacturing a hydrogen sensor, the method comprising the steps of:
   disposing a thin film made of a transition metal or an alloy thereof on a surface of an elastic substrate;
   applying a tensile force in a repetitive manner to the elastic substrate to form a nanocrack on the thin film disposed on the surface of the elastic substrate; and
   injecting hydrogen gas into the formed nanocrack and then removing the hydrogen gas to form a nanogap,
   wherein the tensile force in the step of forming a nanocrack is applied to an extent that the elastic substrate has a tensile strain of 25% to 100%.

2. The method of claim 1, wherein the formed nanogap ranges in width from 30 nm to 200 nm.

3. The method of claim 1, wherein the thin film disposed on the surface of the elastic substrate is 10 nm or more in thickness.

4. The method of claim 1, wherein the thin film disposed on the surface of the elastic substrate is be 20 nm or more in thickness.

5. The method of claim 1, wherein the transition metal is at least one selected from the group consisting of Pd, Pt, Ni, Ag, Ti, Fe, Zn, Co, Mn, Au, W, In, and Al.

6. The method of claim 1, wherein the alloy is at least one selected from the group consisting of Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ag, Pt—Ti, Fe—Pt, Pt—Zn, Pt—Co, Pt—Mn, and Pt—Au, Pt—W.

7. The method of claim 1, wherein the transition metal is Pd and the alloy is a Pd-based alloy.

8. The method of claim 1, wherein the elastic substrate uses a natural rubber, a synthetic rubber, or a polymer.

9. The method of claim 8, wherein the synthetic rubber is any one selected from the group consisting of a butadiene-based rubber, an isoprene-based rubber, a chloroprene-based rubber, a nitrile-based rubber, a polyurethane-based rubber, and a silicone-based rubber.

10. The method of claim 9, wherein the silicone-based rubber is PDMS (polydimethylsiloxane).

11. The method of claim 10, wherein the PDMS is prepared after being cured at 150 to 200° C. for 5 minutes to 10 minutes or by being cured at 10 to 25° C. for 24 hours to 48 hours and then at 50 to 75° C. for 30 minutes to 240 minutes.

12. The method of claim 1, wherein the elastic substrate has a Young's modulus of 0.5 MPa to 2.6 MPa, a tensile strength of 5 MPa to 7 MPa, an elongation of 100% to 200%, and a coefficient of thermal expansion of 270 to 340 ppm/° C.

13. The method of claim 1, wherein the elastic substrate has a Young's modulus of 2.5 MPa to 4.0 MPa, a tensile strength of 3 MPa to 5 MPa, an elongation of 100% to 200%, and a coefficient of thermal expansion of 200 to 250 ppm/° C.

14. The method of claim 1, wherein the tensile force is applied 12 to 24 times repetitively in the step of forming a nanocrack.

15. A hydrogen sensor manufactured according to claim 1.

* * * * *